United States Patent
Okamoto

(10) Patent No.: US 12,281,061 B2
(45) Date of Patent: Apr. 22, 2025

(54) OLEFIN PRODUCTION METHOD

(71) Applicant: Sumitomo Chemical Company, Limited, Tokyo (JP)

(72) Inventor: Yuki Okamoto, Chiba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 18/021,978

(22) PCT Filed: Aug. 11, 2021

(86) PCT No.: PCT/JP2021/029688
§ 371 (c)(1),
(2) Date: Feb. 17, 2023

(87) PCT Pub. No.: WO2022/039094
PCT Pub. Date: Feb. 24, 2022

(65) Prior Publication Data
US 2023/0357105 A1 Nov. 9, 2023

(30) Foreign Application Priority Data
Aug. 20, 2020 (JP) .................................. 2020-139554

(51) Int. Cl.
*C07C 4/06* (2006.01)
*B01J 29/70* (2006.01)
*B01J 29/90* (2006.01)
*B01J 38/12* (2006.01)

(52) U.S. Cl.
CPC ............. *C07C 4/06* (2013.01); *B01J 29/7003* (2013.01); *B01J 29/90* (2013.01); *B01J 38/12* (2013.01); *C07C 2529/70* (2013.01)

(58) Field of Classification Search
CPC .. B01J 29/70; B01J 29/90; B01J 38/12; C07C 4/06
See application file for complete search history.

(56) References Cited

U.S. PATENT DOCUMENTS

| | | | |
|---|---|---|---|
| 3,702,886 A | * | 11/1972 | Argauer ................. C10G 11/05 423/326 |
| 2007/0203517 A1 | | 8/2007 | Williams et al. |
| 2007/0255308 A1 | | 11/2007 | Williams et al. |
| 2007/0299387 A1 | | 12/2007 | Williams et al. |
| 2008/0045803 A1 | | 2/2008 | Williams et al. |
| 2008/0215089 A1 | | 9/2008 | Williams et al. |
| 2010/0200460 A1 | | 8/2010 | Brosten et al. |
| 2011/0066173 A1 | | 3/2011 | Williams et al. |
| 2011/0118545 A1 | | 5/2011 | Williams et al. |
| 2012/0165583 A1 | | 6/2012 | Garforth et al. |
| 2014/0228204 A1 | | 8/2014 | Narayanaswamy et al. |
| 2014/0228205 A1 | | 8/2014 | Narayanaswamy et al. |
| 2014/0228606 A1 | * | 8/2014 | Narayanaswamy ..... B01J 29/40 585/241 |
| 2015/0105629 A1 | | 4/2015 | Williams et al. |
| 2019/0270939 A1 | | 9/2019 | Javeed et al. |

FOREIGN PATENT DOCUMENTS

| | | |
|---|---|---|
| CN | 102458656 A | 5/2012 |
| JP | 2002121318 A | 4/2002 |
| JP | 2010504154 A | 2/2010 |
| JP | 2010526179 A | 7/2010 |
| JP | 2016513147 A | 5/2016 |
| JP | 2016514170 A | 5/2016 |
| JP | 2017137347 A | 8/2017 |
| JP | 2019532118 A | 11/2019 |

OTHER PUBLICATIONS

Uemichi et al., "Catalytic Degradation of Polyolefins into Lower Olefins," Fine Chemical, vol. 46, No. 12, pp. 44-51 (2017), cited in specification.
Santos et al., "A catalytic reactive distillation approach to high density polyethylene pyrolysis—Part 1—Light olefin production," Chemical Engineering Journal, vol. 378, pp. 1-9 (2019).

* cited by examiner

*Primary Examiner* — Sharon Pregler
(74) *Attorney, Agent, or Firm* — Panitch Schwarze Belisario & Nadel LLP

(57) ABSTRACT

An olefin production method is provided involves a step of catalytically cracking a raw material containing at least a polyolefin and an organochlorine compound in the presence of a zeolite catalyst having a sodium atom content of less than 0.1% by mass. This method improves olefin yield.

13 Claims, No Drawings

OLEFIN PRODUCTION METHOD

CROSS-REFERENCE TO RELATED APPLICATIONS

This application is a Section 371 of International Application No. PCT/JP2021/029688, filed Aug. 11, 2021, which was published in the Japanese language on Feb. 24, 2022 under International Publication No. WO 2022/039094 A1, which claims priority under 35 U.S.C. § 119 (b) to Japanese Application No. 2020-139554, filed Aug. 20, 2020, the disclosures of which are incorporated herein by reference in their entireties.

The present invention relates to an olefin production method and a method for regenerating a catalyst used in the production method.

BACKGROUND ART

Main raw materials of the petrochemical industry are lower olefins such as ethylene and propylene obtained by decomposition and reforming of naphtha, and aromatic hydrocarbons such as benzene, toluene, and xylene. A wide variety of chemical products are synthesized using these as starting materials. Among them, plastics are widely used from industrial products to daily products because they have excellent properties as materials, such as the largest production amount, light weight, excellent corrosion resistance, and moldability. As a result, the amount of waste plastic to be discharged is enormous.

Non-Patent Document 1 describes a chemical recycling technique for efficiently decomposing polyethylene into petrochemical raw materials. Specifically, a method for obtaining olefins having 2 to 5 carbon atoms by catalytically cracking polyethylene using an MFI zeolite containing sodium atoms is described.

PRIOR ART DOCUMENTS

Non-Patent Document

Non-Patent Document 1: Monthly Fine Chemicals (Vol. 46 No. 12, December 2017)

SUMMARY OF THE INVENTION

Problems to be Solved by the Invention

However, in the method described in Non-Patent Document 1, the yield of olefins having 2 to 3 carbon atoms to be obtained is not necessarily sufficient. Therefore, the present invention provides an olefin production method with excellent yield of olefins having 2 to 3 carbon atoms.

Means for Solving the Problems

The present invention provides the following [1] to [14].
[1] An olefin production method, including a step of catalytically cracking a raw material containing at least a polyolefin and an organochlorine compound in the presence of a zeolite catalyst having a sodium content of less than 0.1% by mass.
[2] The olefin production method according to [1], in which the zeolite catalyst is an MFI zeolite catalyst.
[3] The olefin production method according to [1] or [2], in which the zeolite catalyst has a Si/Al ratio of 100 or more.
[4] The olefin production method according to [1] or [2], in which the zeolite catalyst has a Si/Al ratio of 300 or more.
[5] The olefin production method according to [1], in which the olefins are olefins having 2 to 3 carbon atoms.
[6] The olefin production method according to any one of [1] to [5], in which the zeolite catalyst has a sodium content of less than 0.05% by mass.
[7] The olefin production method according to any one of [1] to [6], in which the organochlorine compound contains at least one of polyvinyl chloride and polyvinylidene chloride.
[8] The olefin production method according to [7], in which the raw material has a chlorine atom content of 10% by mass or less.
[9] The olefin production method according to any one of [1] to [8], further including a step of thermally decomposing the raw material before the step of catalytically cracking.
[10] The olefin production method according to any one of [1] to [9], further including a step of vaporizing the raw material before the step of catalytically cracking, in which the step of catalytically cracking is a step of catalytically cracking the raw material in a gaseous state.
[11] The olefin production method according to any one of [1] to [10], in which the step of catalytically cracking is performed at 450° C. or more and 600° C. or less.
[12] The olefin production method according to any one of [1] to [11], in which the zeolite catalyst is a regenerated catalyst.
[13] A method for regenerating a catalyst, including a step of calcining the spent zeolite catalyst used in the olefin production method according to any one of [1] to [11] in an atmosphere containing 1% by volume to 50% by volume of oxygen to obtain a regenerated catalyst.
[14] An olefin production method, including a step of catalytically cracking a raw material containing a polyolefin in the presence of a regenerated catalyst regenerated by the regeneration method according to [13].

Effect of the Invention

According to the present invention, it is possible to provide a production method with excellent yield of olefins having 2 to 3 carbon atoms. Further, according to the present invention, it is possible to provide a catalyst regeneration method capable of regenerating a regenerated catalyst having high catalyst performance after regeneration from the spent zeolite catalyst used in the production method by a simple method.

MODE FOR CARRYING OUT THE INVENTION

1. Olefin Production Method

The olefin production method according to the present invention includes a step of catalytically cracking a raw material containing least a polyolefin and an organochlorine compound in the presence of a zeolite catalyst having a sodium content of less than 0.1% by mass. Hereinafter, the olefin production method of the present embodiment will be specifically described.

Step of Catalytic Cracking (Catalytic Cracking Step)

Raw Material

A raw material applicable to the olefin production method of the present embodiment contains at least a polyolefin and an organochlorine compound.

Specific examples of the polyolefin contained as a raw material include polyolefin-based plastics such as polyethylene, polypropylene, polybutene, an ethylene-vinyl acetate copolymer, an ethylene-methyl acrylate copolymer, an ethylene-methyl methacrylate copolymer, an ethylene-propylene copolymer, and an ethylene-α-olefin copolymer, and mixtures of two or more thereof. Among them, polyethylene, polypropylene, and an ethylene-propylene copolymer are preferable.

In addition to the polyolefin-based plastic, the raw material may contain other components such as polystyrene, polyamide, polycarbonate, polyurethane, polyester, polymethyl methacrylate, an acrylonitrile-styrene copolymer, an acrylonitrile-butadiene-styrene copolymer, natural rubber, and synthetic rubber.

Specific examples of the organochlorine compound contained as a raw material include polyvinyl chloride (PVC) and polyvinylidene chloride (PVDC). The organochlorine compound preferably contains at least one of polyvinyl chloride and polyvinylidene chloride.

In the olefin production method of the present embodiment, the upper limit of chlorine atom content that may be contained in the raw material is about 30% by mass, and from the viewpoint of the intended yield of olefin, the raw material preferably has a chlorine atom content of 10% by mass or less.

The raw material may include, for example, industrial products such as compact produced using the above-described polyolefins, organochlorine compounds, and other components. Specific examples of the industrial product include plastic container packaging collected by the Container and Packaging Recycling Law.

The raw material may be in a solid state like the compact described above. The raw material may be used by changing the state of the solid industrial product to a liquid state and/or a gaseous state, and may be, for example, a liquid and/or gaseous mixture of the above-mentioned. polyolefin, organochlorine compound, and other components.

Zeolite Catalyst

Examples of the zeolite catalyst used in the present embodiment include beta zeolite, faujasite zeolite, L zeolite, ferrierite zeolite, mordenite zeolite, and MFI zeolite, and a zeolite catalyst composed of MFI zeolite is preferable. The zeolite catalyst of the present embodiment has a sodium content of less than 0.1% by mass. The sodium content in the zeolite catalyst of the present embodiment is more preferably less than 0.05% by mass from the viewpoint of the intended yield of olefin.

The zeolite catalyst used in the present embodiment may usually contain silicon atoms, aluminum atoms, oxygen atoms, and hydrogen atoms as atoms other than sodium atoms. The zeolite catalyst may also contain atoms such as titanium atoms, chromium atoms, manganese atoms, iron atoms, cobalt atoms, nickel atoms, copper atoms, ruthenium atoms, rhodium atoms, palladium atoms, silver atoms, iridium atoms, platinum atoms, boron atoms, nitrogen atoms, magnesium atoms, phosphorus atoms, zinc atoms, and gallium atoms.

Here, the ratio of the number of moles of silicon atoms to the number of moles of aluminum atoms (Si/Al ratio) of the zeolite catalyst is preferably 100 or more, and more preferably 300 or more, from the viewpoint of improving the intended yield of olefin.

The sodium content and the Si/Al ratio of the zeolite catalyst can be calculated by analyzing the zeolite catalyst according to conventionally known ICP emission spectrometry.

Here, the MFI type zeolite means a crystalline aluminosilicate having an MFI structure in the structure code of IZA (International Zeolite Association). Specific examples of the MFI zeolite include $H^+$-ZSM-5, $NH_4^+$-ZSM-5, $Na^+$-GSM-5, and $Ca^{2+}$-ZSM-5. The MFI zeolite can be prepared by any suitable method conventionally known method, and commercially available $H^+$-ZSM-5 may be used. The MFI zeolite can be confirmed by analysis by X-ray diffraction analysis.

Hereinafter, a method for producing the zeolite catalyst used in the present embodiment will be described. The zeolite catalyst used in the present embodiment can be produced by a production method including a step of preparing a mixture containing a silicon source, an aluminum source, a structure-directing agent and an alkali metal source, and crystallizing the mixture to obtain zeolite. Here, the "structure-directing agent" refers to a substance for imparting a pore structure to zeolite.

As the silicon source, a conventionally known silicon source used for producing various zeolites can be used. Specific examples of the silicon source include tetraethyl orthosilicate, colloidal silica, silica gel dry powder, silica hydrogel, and sodium silicate.

As the aluminum source, a conventionally known aluminum source used for the production of various zeolites can be used. Specific examples of the aluminum source include aluminum nitrate, aluminum chloride, sodium aluminate, aluminum hydroxide, and aluminum alkoxide. Among these aluminum sources, aluminum nitrate or sodium aluminate as preferable.

The type of the structure-directing agent that can be used in the present embodiment is not particularly limited. As the structure-directing agent, conventionally known structure-directing agents such as organic ammonium salts and amines generally used for synthesis of zeolite can be used.

Specific examples of the structure-directing agent include tetrapropylammonium salt, tetraethylammonium salt, tetramethylammonium salt, benzyltrimethylammonium salt, tetrahutylammonium salt, propanolamine, ethanolamine, n-proplyamine, morpholine, 1,5-diaminopentane, 1,6-diaminohexane, dipropylenetetramine, and triethylenetetramine. Among these structure-directing agents, a tetrapropylammonium salt (tetrapropylammonium hydroxide) is preferable.

Examples of the alkali metal source include alkali metal hydroxides, alkali metal chlorides, alkali metal bromides, and alkali metal sulfides. Specific examples of the alkali metal include sodium and potassium.

When the alkali metal is sodium, specific examples of the sodium source include sodium hydroxide, sodium nitrate, sodium chloride, sodium bromide, sodium sulfate, sodium silicate, sodium aluminate, and compounds containing sodium as a counter cation.

When the alkali metal is potassium, specific examples of the potassium source include potassium hydroxide, potassium nitrate, potassium chloride, potassium bromide, potassium sulfate, potassium silicate, potassium aluminate, and compounds containing potassium as a counter cation.

In the mixture, the ratio of the number of moles of silicon atoms to the number of moles of aluminum atoms (Si/Al ratio) is preferably 100 or more, and more preferably 300 or more. The ratio may be 10,000 or less, and is preferably 2,500 or less.

In addition, the ratio of the number of moles of each component in the mixture to the number of moles of silicon atoms preferably satisfies the following requirements.

Structure-directing agent: 0.02 or more and 5.0 or less
Alkali metal source: 0.01 or more and 0.2 or less
Water: 2 or more and 100 or less Furthermore, the ratio of the number of moles of each component in the mixture to the number of moles of silicon atoms more preferably satisfies the following requirements.

Structure-directing agent: 0.05 or more and 2.0 or less
Alkali metal source: 0.04 or more and 0.3 or less
Water: 5 or more and 50 or less Hereinafter, specific steps will be described.

First, a mixture obtained by stirring the above components (mixture) at normal temperature for 1 hour to 48 hours (for example, 18 hours) is placed in a sealed pressure vessel (autoclave), and the mixture is treated at a temperature of 100° C. to 200° C. in an autoclave over 1 hour to 120 hours, whereby a precursor of zeolite can be prepared.

After completion of the crystallization, a step of sufficiently cooling a mixture (suspension) containing a precursor of the prepared zeolite with ice water or the like, and after completion of the cooling, removing the supernatant by solid-liquid separation (for example, centrifugation), and further washing with a sufficient amount of pure water to perform solid-liquid separation is repeated until the pH of the removed supernatant becomes 8 or less.

Next, the resultant is dried at a temperature of 100° C. to 150° C. (for example, 120° C.) for 1 hour to 48 hours (for example, 8 hours). Thereafter, calcination may be performed at a temperature of about 400° C. to 700° C. (for example, 550° C.) for 1 hour to 48 hours (for example, 7 hours).

Zeolite (e.g., MFI zeolite) can be obtained by the above step.

The zeolite prepared as described above contains a relatively large amount of sodium or potassium contained in the alkali metal source. Therefore, in order to obtain the zeolite catalyst used in the present embodiment, it is usually necessary to remove the alkali metal in the zeolite.

Examples of the method for removing the alkali metal in the zeolite include a method in which the zeolite is brought into contact with an aqueous solution of an ammonium salt.

Examples of the ammonium salt include ammonium salts of inorganic acids such as ammonium sulfate, ammonium hydrogen sulfate, ammonium carbonate, ammonium hydrogen carbonate, diammonium hydrogen phosphate, ammonium dihydrogen phosphate, ammonium phosphate, ammonium hydrogen pyrophosphate, ammonium pyrophosphate, ammonium chloride, and ammonium nitrate, ammonium salts of organic acids such as ammonium acetate, and the like. Among them, ammonium sulfate, ammonium chloride, and ammonium nitrate are preferably used.

Specifically, in this step, a step of mixing an aqueous solution of an ammonium salt with zeolite to bring into contact with each other at a temperature of 50° C. to 200° C. over 1 to 48 hours is further repeated once or more as necessary, so that the content (for example, the sodium atom content) of the alkali metal can be adjusted (reduced) to a desired content.

Next, the mixture is sufficiently cooled to perform solid-liquid separation, washed with a sufficient amount of pure water, and dried at an arbitrary temperature of 60° C. to 150° C.

Thereafter, calcination is preferably performed at a temperature of about 400° C. to 700° C. (for example, 550° C.) for 1 hour to 48 hours (for example, 5 hours).

By preparing the zeolite catalyst as described above, it is possible to obtain the zeolite catalyst of the present embodiment in which sodium atoms as alkali metal are reduced to a sodium content of less than 0.1% by mass.

The temperature in the catalytic cracking step (contact temperature $T^2$) is usually 400° C. to 700° C., and preferably 450° C. to 600° C. (450° C. or more and 600° C. or less).

The pressure in the catalytic cracking step (contact pressure $P^2$) is usually 0 MPaG to 5 MPaG, and preferably 0 MPaG to 0.5 MPaG.

In the catalytic cracking step, an inert gas such as water vapor, nitrogen gas, or $CO_2$ gas may coexist.

The catalytic cracking step can be performed using any suitable conventionally known reaction vessel. Examples of the material of the reaction vessel include quartz glass, carbon steel, stainless steel, an Inconel alloy, a Hastelloy alloy, an Incoloy alloy, and a Monel alloy.

The olefins obtained in the catalytic cracking step are usually olefins having 2 to 5 carbon atoms, such as ethylene, propylene, or butenes, and preferably olefins having 2 to 3 carbon atoms.

The zeolite catalyst used in the catalytic cracking step may be a regenerated catalyst (details will be described later). That is, the olefin production method of the present embodiment may include a step of catalytically cracking a raw material containing a polyolefin in the presence of a regenerated catalyst.

Step of Thermal Decomposition (Thermal Decomposition Step)

The olefin production method of the present embodiment preferably further includes a step of thermally decomposing a raw material before the catalytic cracking step described above from the viewpoint of further improving the yield of olefin, and the catalytic cracking step is preferably a step of catalytically cracking a raw material in a gaseous state, a liquid state, or a mixed state thereof.

The thermal decomposition step in the olefin production method of the present embodiment can be performed using any suitable apparatus known in the related art by adopting conditions corresponding to the selected raw material and the components contained in the raw material.

The thermal decomposition step of the present embodiment can be performed using a vessel different from the vessel is which the catalytic cracking step described above is performed. In addition, the thermal decomposition step and the catalytic cracking step of the present embodiment may be continuously performed using the same reaction vessel.

Thermal decomposition temperature $T^1$ in the thermal decomposition step of the present embodiment and the contact temperature $T^2$ in the catalytic cracking step preferably satisfy conditions represented by the following formula.

$$0° C. \leq T^2 - T^1 \leq 200° C.$$

The thermal decomposition temperature $T^1$ in the thermal decomposition step is usually 350° C. to 550° C. and preferably 400° C. to 500° C.

Thermal decomposition pressure $P^1$ in the thermal decomposition step is usually 0 MPaG to 5 MPaG, and preferably 0 MPaG to 0.5 MPaG. Also, the relationship between the thermal decomposition pressure $P^1$ and the contact pressure $P^2$ is preferably $P^1 \geq P^2$.

In the Thermal decomposition step, an inert gas such as water vapor, nitrogen gas, or $CO_2$ gas may coexist.

The thermal decomposition step can be performed using any suitable conventionally known reaction vessel. Examples of the material of the reaction vessel include quartz glass, carbon steel, stainless steel, an Inconel alloy, a Hastelloy alloy, an Incoloy alloy, and a Monel alloy.

The thermal decomposition product of the raw material obtained by the thermal decomposition step usually contains hydrocarbon having about 1 to 50 carbon atoms, hydrogen, and the like in a liquid state, a gaseous state, or a mixed state thereof.

Step of vaporizing raw material (vaporization step)

In the olefin production method of the present embodiment, it is preferable to further include a vaporization step before the catalytic cracking step, and the catalytic cracking step is a step of catalytically cracking a raw material in a gaseous state.

The vaporization step is the olefin production method of the present embodiment can be performed using any suitable apparatus known in the related art by adopting conditions corresponding to the selected raw material and the components contained in the raw material.

The vaporization step of the present embodiment can be performed using the vessel in which the catalytic cracking step described above is performed. In addition, the vaporization step and the catalytic cracking step of the present embodiment may be continuously performed using the same reaction vessel.

Temperature $T^3$ in the vaporization step is usually 350° C. to 550° C., and preferably 400° C. to 500° C.

Pressure $P^3$ in the vaporization step is usually 0 MPaG to 5 MPaG, and preferably 0 MPaG to 0.5 MPaG. Within such a range, the raw material can be efficiently made into a gaseous state.

In the vaporization step, an inert gas such as water vapor, nitrogen gas, or $CO_2$ gas may coexist.

The vaporization step can be performed using any suitable conventionally known reaction vessel. Examples of the material of the reaction vessel include quartz glass, carbon steel, stainless steel, an Inconel alloy, a Hastelloy alloy, an Incoloy alloy, and a Monel alloy.

The decomposition product of the raw material obtained by the vaporization step contains hydrocarbon having about 1 to 50 carbon atoms, hydrogen, and the like in a gaseous state.

In the olefin production method of the present embodiment, the thermal decomposition step, the vaporization step, and the catalytic cracking step described above may be integrally and continuously performed in this order.

According to the olefin production method of the present embodiment, for example, in the case of using a raw material containing an organochlorine compound that is inevitably contained in a raw material containing a polyolefin such as a food packaging container and conventionally can be a catalyst poison and thus was needs to be removed in advance, the olefin can be efficiently produced without removing the organochlorine compound in advance. In performing the olefin production method of the present embodiment, the organochlorine compound may be removed from the raw material in advance.

2. Method for Regenerating Catalyst

The zeolite catalyst used in the catalytic cracking step of the present embodiment may be a regenerated catalyst. That is, the olefin production method of the present embodiment can be performed by applying a raw material containing a polyolefin (an organochlorine compound may be further contained) to the catalytic cracking step in the presence of a regenerated catalyst obtained by regenerating the spent zeolite catalyst used in the olefin production method described above.

Hereinafter, a method for regenerating a catalyst of the present embodiment will be specifically described.

The method for regenerating a catalyst of the present embodiment includes a step of obtaining a regenerated catalyst by calcinating a catalyst in an atmosphere containing 1 vol % to 50 vol % of oxygen.

The step of obtaining a regenerated catalyst is preferably performed in an atmosphere containing oxygen in a range of 1 vol % to 50 vol %, and more preferably performed in an atmosphere containing oxygen in a range of 5 vol % to 30 vol %.

The step of obtaining a regenerated catalyst can be performed, for example, in an air atmosphere, a nitrogen gas atmosphere, an argon gas atmosphere, a carbon dioxide gas atmosphere, or a mixed gas atmosphere thereof while adjusting the oxygen concentration in the atmosphere by any suitable conventionally known method.

The temperature in the step of obtaining a regenerated catalyst is preferably in the range of 400° C. to 700° C. (for example, 550° C.) and more preferably in the range of 450° C. to 600° C.

The treatment time in the step of obtaining a regenerated catalyst is preferably 30 minutes to 48 hours (for example, 5 hours), and more preferably 1 hour to 24 hours.

When the regenerated catalyst obtained by the method for regenerating a catalyst is applied to the olefin production method of the present embodiment, the regenerated catalyst can be used in the same manner as the "zeolite catalyst" that is not used for the catalytic cracking reaction of polyolefin without particularly adjusting conditions such as temperature, treatment time, and atmosphere.

EXAMPLES

Hereinbelow, the present invention will be described in detail with reference to Examples. The present invention is not limited at all by the following examples.

Reference Example 1 Preparation of Zeolite Catalyst A

Aluminum nitrate nonahydrate (0.29 g), a 20.3% by mass tetrapropylammonium hydroxide aqueous solution (76.8 g), sodium hydroxide (0.77 g) and tetraethyl orthosilicate (64.0 g) were added to a 400 mL PTFE vessel equipped with a stirrer, and the mixture was stirred at normal temperature for 18 hours to obtain a mixture. Thereafter, ion-exchanged water (56.6 g) was added to the mixture, and the entire amount was transferred to a stainless steel (SUS) autoclave equipped with a 200 mL PTFE inner cylinder vessel.

In the mixture, the ratio of the number of moles of silicon atoms to the number of moles of aluminum atoms was 400, the ratio of the number of moles of tetrapropylammonium hydroxide to the number of moles of silicon atoms was 0.56, the ratio of the number of moles of sodium atoms to the number of moles of silicon atoms was 0.06, and the ratio of the number of moles of water to the number of moles of silicon atoms was 13.

The mixture was heat-treated at a temperature of 170° C. for 24 hours in an autoclave, and then cooled with ice water. After cooling, the mixture (suspension) in the cylindrical vessel was centrifuged, and the supernatant was removed, thereby obtaining a precursor of zeolite.

Water was added to the obtained precursor of zeolite to form a suspension again, and an operation of removing the supernatant by further centrifugation was repeated until the pH of the supernatant reached 8 or less to form a solid again.

The obtained solid was dried at 120° C. for 8 hours. The dried solid was pulverized in a mortar and further calcined at 550° C. for 7 hours using a muffle furnace, thereby obtaining zeolite 1 (14.1 g).

The zeolite 1 (6.6 g) and a 0.5 M aqueous ammonium nitrate solution. (300 mL) were added to a 500 mL resin vessel, and the mixture was allowed to stand at a temperature of 60° C. for 6 hours. Thereafter, the resulting mixture was subjected to suction filtration using a Buchner funnel, and a solid was collected.

The collected solid and a 0.5 M aqueous ammonium nitrate solution (330 mL) were added to a flask, and the mixture was allowed to stand at a temperature of 60° C. for 12 hours. Thereafter, the resulting mixture was subjected to suction filtration using a Buchner funnel, and a solid was collected.

Next, the collected solid and a 0.5 M aqueous ammonium nitrate solution (330 mL) were added to a flask, and the mixture was allowed to stand at a temperature of 60° C. for 6 hours. Thereafter, the resulting mixture was subjected to suction filtration using a Buchner funnel, and a solid was collected. The collected solid was washed with water (500 mL) and dried at 90° C. for 6 hours to obtain a solid.

The obtained solid was calcined at a temperature of 550° C. for 5 hours in an air atmosphere using a muffle furnace to obtain a powdery zeolite catalyst A (5.1 g).

As a result of analyzing the zeolite catalyst A by ICP emission. spectrometry, the sodium atom content was less than 0.01% by mass, which is the detection lower limit, and the ratio of the number of moles of silicon atoms to the number of moles of aluminum atoms (Si/Al ratio) was 349.

In addition, as a result of analyzing the zeolite catalyst A by an X-ray diffraction analysis method, it was confirmed that the zeolite catalyst A had an MFI structure.

Example 1 Production of Olefin

A raw material that is a mixture of polyethylene (LDPE) (manufactured by Sumitomo Chemical Co., Ltd., trade name: SUMIKATHENE G201F) (1.425 g) that is a polyolefin and polyvinyl chloride (PVC) (manufactured by Shin-Etsu Chemical Co., Ltd., trade name: Shin-Etsu PVC straight polymer TK-1000) (0.075 g) that is an organochlorine compound (weight ratio LDPE: PVC=95:5) was filled in an upstream reaction tube of two glass reaction tubes connected in series, and the zeolite catalyst A (0.3 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the zeolite catalyst A, and then the temperature of the downstream reaction tube was lowered to 525° C.

A step of thermally decomposing the saw material was performed at an electric furnace temperature of the upstream reaction tube of 455° C. while flowing nitrogen gas at a flow rate of 10 N mL/min to obtain a raw material as a thermally decomposed mixture.

Next, a step of catalytically cracking the thermally decomposed raw material was performed. Specifically, this step was performed by introducing the thermally decomposed raw material obtained as described above into the downstream reaction tube set at a temperature $T^2$ of 525° C., and bringing the raw material into contact with the catalyst. The whole amount of the liquid catalytic cracking product obtained 2 hours after the start of heating of the raw material was collected in the cooling trap cooled with ice water, and further the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 37.1% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield. of the olefins having 2 to 3 carbon atoms was calculated to be 34.4% on the basis of the mass of the charged polyethylene. The results are also shown in Table 1.

Finally, the spent zeolite catalyst (spent zeolite catalyst B) was collected from the reaction system.

Example 2 Regeneration of Spent Zeolite Catalyst B (Preparation of Regenerated Catalyst C)

The spent zeolite catalyst B collected in Example 1 was calcined at a temperature of 550° C. for 5 hours in an air atmosphere (oxygen concentration: 21 vol %) using a muffle furnace to obtain a regenerated zeolite catalyst as a regenerated catalyst C.

Example 3 Production of Olefin by Regenerated Catalyst C

Polyethylene (LDPE) (manufactured by Sumitomo Chemical Co., Ltd., trade name: SUMIKATHENE G201F) (1.0 g) was filled is an upstream reaction tube of two glass reaction tubes connected in series as a raw material, and regenerated catalyst C (0.2 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the regenerated catalyst C, then the temperature of the downstream reaction tube was lowered to 525° C.

A step of the rally decomposing the raw material was performed at an electric furnace temperature of the upstream reaction tube of 455° C. while flowing nitrogen gas at a flow rate of 10 N mL/min to obtain a thermally decomposed raw material.

Next, a step of catalytically cracking the thermally decomposed raw material was performed by introducing the thermally decomposed raw material obtained as described above into a downstream reaction tube set at a temperature $T^2$ of 525° C., and bringing the raw material into contact with the regenerated catalyst C. The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield. of olefins having 2 to 3 carbon atoms was 39.0% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 36.8% on the basis of the mass of the charged polyethylene. The results are also shown. in Table 1.

Reference Example 2 Preparation of Zeolite Catalyst D

Aluminum nitrate nonahydrate (1.15 g), a 20.3% by mass tetrapropylammonium hydroxide aqueous solution (76.8 g), sodium hydroxide (0.77 g) and tetraethyl orthosilicate (64.0 g) were added to a 400 mL PTFE vessel equipped with a stirrer, and the mixture was stirred at normal temperature for 18 hours to obtain a mixture. Thereafter, ion-exchanged water (56.6 g) was added to the obtained mixture, and the entire amount was transferred to a SUS autoclave equipped with a 200 mL PTFE inner cylinder vessel.

In the mixture, the ratio of the number of moles of silicon atoms to the number of moles of aluminum atoms was 100, the ratio of the number of moles of tetrapropylammonium hydroxide to the number of moles of silicon atoms was 0.56, the ratio of the number of moles of sodium atoms to the number of moles of silicon atoms was 0.06, and the ratio of the number of moles of water to the number of moles of silicon atoms was 13.

The mixture was heat-treated at a temperature of 170° C. for 24 hours in an autoclave, and then cooled with ice water. After cooling, the mixture (suspension) in the cylindrical vessel was centrifuged, and the supernatant was removed to obtain a precursor of zeolite.

Water was added to the precursor of the obtained zeolite to form a suspension again, and an operation of removing the supernatant by centrifugation was repeated until the pH of the supernatant reached 8 or less to obtain a solid.

The obtained solid was dried at 120° C. for 8 hours. The dried solid was pulverized using a mortar and further calcined at 550° C. and 7 hours using a muffle furnace to obtain zeolite 2 (13.6 g).

The zeolite 2 (6.0 g) and a 0.5 M aqueous ammonium nitrate solution (300 mL) were added to a 500 mL resin vessel, and the mixture was allowed to stand at a temperature of 60° C. for 6 hours. Thereafter, the resulting mixture was subjected to suction filtration using a Buchner funnel, and a solid was collected.

The collected solid and a 0.5 M aqueous ammonium nitrate solution (300 mL) were added to a flask, and the mixture was allowed to stand at a temperature of 60° C. for 12 hours. Thereafter, the resulting mixture was subjected to suction filtration using a Buchner funnel, and a solid was collected.

The collected solid and a 0.5 M aqueous ammonium nitrate solution (300 mL) were added to a flask, and the mixture was allowed to stand at a temperature of 60° C. for 6 hours. Thereafter, the resulting mixture was subjected to suction filtration using a Buchner funnel, and a solid was collected.

The collected solid was washed with water (500 mL) and dried at 90° C. for 6 hours. The obtained solid. was calcined at a temperature of 550° C. for 5 hours in an air atmosphere using a muffle furnace to obtain zeolite 3 (4.6 g).

The obtained zeolite 3 (4.5 g) and a 0.1 M aqueous sodium nitrate solution (450 ml) were added to a 2-necked 500 mL glass re-covers flask equipped with a cooling tube, and the mixture was allowed to stand at a temperature of 100° C. for 2 hours. Thereafter, the resulting mixture was subjected to suction filtration using a Buchner funnel, and a solid was collected.

The collected solid and a 0.1 M aqueous sodium nitrate solution (450 mL) were added to the recovery flask, and the mixture was allowed to stand at a temperature of 100° C. for 2 hours, Thereafter, the resulting mixture was subjected to suction filtration using a Buchner funnel, and a solid was collected. The collected solid was washed with water (300 mL) and dried at a temperature of 110° C. for 12 hours.

The obtained solid was calcined at a temperature of 550° C. for 5 hours in an air atmosphere using a muffle furnace to obtain a powdery zeolite catalyst D (4.1 g).

As a result of analyzing the zeolite catalyst C by ICP emission spectrometry, the sodium atom content was 0.24% by mass, and the ratio of the number of moles of silicon atoms to the number of moles of aluminum atoms (Si/Al ratio) was 85.

In addition, as a result of analyzing the zeolite catalyst D by an X-ray diffraction analysis method, it was confirmed that the zeolite catalyst D had an MFI structure.

Comparative Example 1 Production of Olefin

A raw material that is a mixture of polyethylene (LDPE) (manufactured by Sumitomo Chemical Co., Ltd., trade name: SUMIKATHENE G201F) (1.425 g) that is a polyolefin and Polyvinyl chloride (PVC) (manufactured by Shin-Etsu Chemical Co., Ltd., trade name: Shin-Etsu PVC straight polymer TK-1000 (0.075 g) that is an organochlorine compound. (weight ratio LDPE: PVC=95:5) was filled in an upstream reaction tube of two glass reaction tubes connected in series, and zeolite catalyst (0.3 g) was filled in a downstream reaction tube.

A cooling trap was connected further downstream of the downstream reaction tube, and a 5 L gas bag was connected downstream of the cooling trap.

Nitrogen gas was circulated from the upstream reaction tube at a flow rate of 10 N mL/min, and only the downstream reaction tube was heated at 550° C. for 1 hour to pretreat the zeolite catalyst D, then the temperature of the downstream reaction tube was lowered to 525° C.

A step of thermally decomposing the raw material was performed at an electric furnace temperature of the upstream reaction tube of 455° C. while flowing nitrogen gas at a flow rate of 10 N mL/min to obtain a thermally decomposed raw material. A step of catalytically cracking the thermally decomposed raw material was performed by introducing the thermally decomposed raw material obtained as described above into a downstream reaction tube set at a temperature $T^2$ of 525° C., and bringing the raw material into contact with the zeolite catalyst D.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected. gaseous catalytic cracking product by gas chromatography, the yield of olefins having 2 to 3 carbon atoms was 19.8% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 25.2% on the basis of the mass of the charged polyethylene. The results are also shown in Table 1.

Finally, the spent zeolite catalyst (spent zeolite catalyst E) was collected.

Comparative Example 2 Regeneration of Spent Zeolite Catalyst E (Preparation of Regenerated Catalyst F)

The spent zeolite catalyst E was calcined at a temperature of 550° C. for 5 hours in an air atmosphere using a muffle furnace to obtain a regenerated catalyst F.

Comparative Example 3 Production of Olefin by Regenerated Catalyst F

Polyethylene (LDPE) (manufactured by Sumitomo Chemical Co., Ltd., trade name: SUMIKATHENE G201F) (1.0 g) was filled in an upstream reaction tube of two glass reaction tubes connected in series that is a polyolefin as a raw material, and regenerated catalyst F (0.2 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the regenerated catalyst F, then the temperature of the downstream reaction tube was lowered to 525° C. A step of thermally decomposing the raw material was performed at an electric furnace temperature of the upstream reaction tube of 455° C. while flowing nitrogen gas at a flow rate of 10 N mL/min to obtain a thermally decomposed raw material. A step of catalytically cracking the thermally decomposed raw material was performed by introducing the raw material obtained as described above into a downstream reaction tube set at a temperature $T^2$ of 525° C., and bringing the raw material into contact with the regenerated catalyst F.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction cube and the downstream reaction tube were measured using a balance.

As a result of analysing the collected gaseous catalytic cracking product by gas chromatography, the yield of olefins having 2 to 3 carbon atoms was 26.2% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 30.8% on the basis of the mass of the charged polyethylene. The results are also shown in Table 1.

Reference Example 3 Preparation of Zeolite Catalyst G

Aluminum nitrate nonahydrate (0.30 g), a 22.3% by mass tetrapropylammonium hydroxide aqueous solution. (76.8 g), sodium hydroxide (0.79 g) and tetraethyl orthosilicate (63.4 g) were added to a 400 mL PTFE vessel equipped with a stirrer, and the mixture was stirred at normal temperature for 18 hours to obtain a mixture. Thereafter, ion-exchanged water (56.4 g) was added to the mixture, and the entire amount was transferred to a stainless steel (SUS) autoclave equipped with a 200 mL PTFE inner cylinder vessel.

In the mixture, the ratio of the number of moles of silicon atoms to the number of moles of aluminum atoms was 400, the ratio of the number of moles of tetrapropylammonium hydroxide to the number of moles of silicon atoms was 0.56, the ratio of the number of moles of sodium atoms to the number of moles of silicon. atoms was 0.06, and the ratio of the number of moles of water to the number of moles of silicon atoms was 13.

The mixture was heat-treated at a temperature of 170° C. for 24 hours in an autoclave, and then cooled with ice water. After cooling, the mixture (suspension) in the cylindrical vessel was centrifuged, and the supernatant was removed, thereby obtaining a precursor of zeolite.

Water was added to the obtained precursor of zeolite to form a suspension again, and an operation of removing the supernatant by further centrifugation was repeated until the pH of the supernatant reached 8 or less to form a solid again.

The obtained solid was dried at 120° C. for 8 hours. The dried solid was pulverized in a mortar and further calcined at 550° C. for 6 hours using a muffle furnace, thereby obtaining zeolite 4 (12.5 g).

The zeolite 4 (10.0 g) and a 0.5 M aqueous ammonium nitrate solution (500 mL) were added to a 500 mL resin vessel, and the mixture was allowed to stand at a temperature of 60° C. for 6 hours. Thereafter, the resulting mixture was subjected to suction filtration using a Buchner funnel, and a solid was collected.

The collected solid and a 0.5 M aqueous ammonium nitrate solution (500 mL) were added to a flask, and the mixture was allowed to stand at a temperature of 60° C. for 6 hours. Thereafter, the resulting mixture was subjected to suction filtration using a Buchner funnel, and a solid was collected.

Next, the collected solid and a 0.5 M aqueous ammonium nitrate solution (500 mL) were added to a flask, and the mixture was allowed to stand at a temperature of 60° C. for 6 hours. Thereafter, the resulting mixture was subjected to suction filtration using a Buchner funnel, and a solid was collected. The collected solid was washed with water (750 mL) and dried at 90° C. for 12 hours to obtain a solid.

The obtained solid was calcined at a temperature of 550° C. for 5 hours in an air atmosphere using a muffle furnace to obtain a powdery zeolite catalyst G (7.3 g).

As a result of analyzing the zeolite catalyst G by ICP emission spectrometry, the sodium atom content was 0.03% by mass, and the ratio of the number of moles of silicon atoms to the number of moles of aluminum atoms (Si/Al ratio) was 576.

In addition, as a result of analyzing the zeolite catalyst G by an X-ray diffraction analysis method, it was confirmed that the zeolite catalyst G had an MFI structure.

Example 4 Production of Olefin

A raw material that is a mixture of polyethylene (LDPE) (manufactured by Sumitomo Chemical Co., Ltd., trade name: SUMIKATHENE G201F) (1.425 g) that is a polyolefin and polyvinyl chloride (PVC) (manufactured by Shin-Etsu Chemical Co., Ltd., trade name: Shin-Etsu PVC straight Polymer TK-1000) (0.075 g) that is an organochlorine compound (weight ratio LDPE: PVC=95:5) was filled in an upstream reaction tube of two glass reaction tubes connected in series, and zeolite catalyst G (0.3 g) was filled in a downstream reaction tube.

A cooling trap was connected further downstream of the downstream reaction tube, and a 5 L gas bag was connected downstream of the cooling trap.

Nitrogen gas was circulated from the upstream reaction tube at a flow rate of 10 N mL/min, and only the downstream reaction tube was heated at 550° C. for 1 hour to pretreat the zeolite catalyst G, then the temperature of the downstream reaction tube was lowered to 525° C.

A step of thermally decomposing the raw material was performed at an electric furnace temperature of the upstream reaction tube of 455° C. while flowing nitrogen gas at a flow rate of 10 N mL/min to obtain a thermally decomposed raw material. A step of catalytically cracking the thermally decomposed raw material was performed by introducing the thermally decomposed raw material obtained as described above into a downstream reaction tube set at a temperature $T^2$ of 525° C., and bringing the raw material into contact with the zeolite catalyst G.

The whole amount of the liquid catalytic cracking product obtained 2 hours after the start heating of the raw material was collected in the cooling trap cooled with ice water, and the whole amount of the gaseous catalytic crack product was collected in the gas bag Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 37.0% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 38.8% on the basis of the mass of the charged polyethylene. The results are also shown in Table 1.

Finally, the spent zeolite catalyst (spent zeolite catalyst H) was collected.

Example 5 Regeneration of Spent Zeolite Catalyst H (Preparation of Regenerated Catalyst I)

The spent zeolite catalyst H was calcined at a temperature of 550° C. for 5 hours in an air atmosphere using a muffle furnace to obtain a regenerated catalyst I.

Example 6 Production of Olefin by Regenerated Catalyst I

Polyethylene (LDPE) (manufactured by Sumitomo Chemical Co., Ltd., trade name: SUMIKATHENE G201F) (1.0 g) was filled in an upstream reaction tube of two glass reaction tubes connected in series that is a polyolefin as a raw material, and regenerated catalyst I (0.2 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the regenerated catalyst I, then the temperature of the downstream reaction tube was lowered to 525° C. A step of thermally decomposing the raw material was performed at an electric furnace temperature of the upstream reaction tube of 455° C. while flowing nitrogen gas at a flow rate of 10 N mL/min to obtain a thermally decomposed raw material.

A step of catalytically cracking the thermally decomposed raw material was performed by introducing the raw material obtained as described above into a downstream reaction tube set at a temperature $T^2$ of 525° C., and bringing the raw material into contact with the regenerated catalyst I.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction cube and the downstream reaction tube were measured using a balance.

As a result of analyzing the collected gaseous catalytic cracking product by gas chromatography, the yield of olefins having 2 to 3 carbon atoms was 37.5% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 38.6% on the basis of the mass of the charged polyethylene. The results are also shown in Table 1.

Reference Example 4 Preparation of Zeolite Catalyst J

Aluminum nitrate nonahydrate (0.122 g), a 20.3% by mass tetrapropylammonium hydroxide aqueous solution (76.8 g), sodium hydroxide (0.77 g) and tetraethyl orthosilicate (64.0 g) were added to a 400 mL PTFE vessel equipped with a stirrer, and the mixture was stirred at normal temperature for 18 hours to obtain a mixture. Thereafter, ion-exchanged water (56.6 g) was added to the mixture, and the entire amount was transferred to a stainless steel (SUS) autoclave equipped with a 200 mL PTFE inner cylinder vessel.

In the mixture, the ratio of the number of moles of silicon atoms to the number of moles of aluminum atoms was 1000, the ratio of the number of moles of tetrapropylammonium hydroxide to the number of moles of silicon atoms was 0.56, the ratio of the number of moles of sodium atoms to the number of moles of silicon atoms was 0.06, and the ratio of the number of moles of water to the number of moles of silicon atoms was 13.

The mixture was heat-treated at a temperature of 170° C. for 24 hours in an autoclave, and then cooled with ice water. After cooling, the mixture (suspension) in the cylindrical vessel was centrifuged, and the supernatant was removed, thereby obtaining a precursor of zeolite.

Water was added to the obtained precursor of zeolite to form a suspension again, and an operation of removing the supernatant by further centrifugation was repeated until the pH of the supernatant reached 8 or less to form a solid again.

The obtained solid was dried at 120° C. for 8 hours. The dried solid was pulverized in a mortar and further calcined at 550° C. for 7 hours using a muffle furnace, thereby obtaining zeolite 5 (14.2 g).

The zeolite 5 (6.6 g) and a 0.5 M aqueous ammonium nitrate solution (300 mL) were added to a 500 mL resin vessel, and the mixture was allowed to stand at a temperature of 60° C. for 5 hours. Thereafter, the resulting mixture was subjected to suction filtration using a Buchner funnel, and the collected solid was dried at 90° C. for 1 hour.

The dried. solid. and a 0.5 M aqueous ammonium nitrate solution (330 ml) were added to a flask, and the mixture was allowed to stand at a temperature of 60° C. for 6 hours. Thereafter, the resulting mixture was subjected to suction filtration using a Buchner funnel, and a solid was collected.

Next, the collected solid and a 0.5 M aqueous ammonium nitrate solution (330 mL) were added to a flask, and the mixture was allowed to stand at a temperature of 60° C. for 12 hours. Thereafter, the resulting mixture was subjected to suction filtration using a Buchner funnel, and a solid was collected. The collected solid was washed with water (500 mL) and dried at 90° C. for 6 hours to obtain a solid.

The obtained solid was calcined at a temperature of 550° C. for 5 hours in an air atmosphere using a muffle furnace to obtain a powdery zeolite catalyst J (5.5 g).

As a result of analyzing the zeolite catalyst J by ICP emission spectrometry, the sodium atom content was less than 0.01% by mass, which is the detection lower limit, and the ratio of the number of moles of silicon atoms to the number of moles of aluminum atoms (Si/Al ratio) was 1249.

In addition, as a result of analyzing the zeolite catalyst J by an X-ray diffraction analysis method, it was confirmed that the zeolite catalyst J had an MFI structure.

Example 7 Production of Olefin

A raw material that is a mixture of polyethylene (LDPE) (manufactured by Sumitomo Chemical Co., Ltd., trade name: SUMIKATHENE G201F) (1.425 g) that is a polyolefin and polyvinyl chloride (PVC) (manufactured by Shin-Etsu Chemical Co., Ltd., trade name: Shin-Etsu PVC straight polymer TK-1000) (0.075 g) that is an organochlorine compound (weight ratio LDPE: PVC=95:5) was filled in an upstream reaction tube of two glass reaction tubes connected in series, and zeolite catalyst J (0.3 g) was filled in a downstream reaction tube.

A cooling trap was connected. further downstream of the downstream reaction tube, and a 5 L gas bag was connected downstream of the cooling trap.

Nitrogen gas was circulated from the upstream reaction tube at a flow rate of 10 N mL/min, and only the downstream reaction tube was heated at 550° C. for 1 hour to pretreat the zeolite catalyst J, then the temperature of the downstream reaction tube was lowered to 525° C.

A step of thermally decomposing the raw material was performed at an electric furnace temperature of the upstream reaction tube of 455° C. while flowing nitrogen gas at a flow rate of 10 N mL/min to obtain a thermally decomposed raw material. A step of catalytically cracking the thermally decomposed raw material was performed by introducing the thermally decomposed raw material obtained as described above into a downstream reaction tube set at a temperature $T^2$ of 525° C., and bringing the raw material into contact with the zeolite catalyst J.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 31.2% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 34.5% on the basis of the mass of the charged polyethylene. The results are also shown in Table 1.

Finally, the spent zeolite catalyst (spent zeolite catalyst K) was collected.

Example 8 Regeneration of Spent Zeolite Catalyst K (Preparation of Regenerated Catalyst L)

The spent zeolite catalyst K was calcined at a temperature of 550° C. for 5 hours in an air atmosphere using a muffle furnace to obtain a regenerated catalyst L.

Example 9 Production of Olefin by Regenerated Catalyst L

Polyethylene (LDPE) (manufactured by Sumitomo Chemical Co., Ltd., trade name: SUMIKATHENE G201F) (1.0 g) was filled in an upstream reaction tube of two glass reaction tubes connected in series that is a polyolefin as a raw material, and regenerated catalyst L (0.2 was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream. reaction tube was heated at 50° C. for 1 hour to perform pretreatment of the regenerated catalyst L, then the temperature of the downstream reaction tube was lowered to 525° C. A step of thermally decomposing the raw material was performed at an electric furnace temperature of the upstream reaction tube of 455° C. while flowing nitrogen gas at a flow rate of 10 N mL/min to obtain a thermally decomposed raw material.

A step of catalytically cracking the thermally decomposed raw material was performed by introducing the raw material obtained as described above into a downstream reaction tube set at a temperature $T^2$ of 525° C., and bringing the raw material into contact with the regenerated catalyst L.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 29.8% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to carbon atoms was calculated to be 33.2% on the basis of the mass of the charged polyethylene. The results are also shown in Table 1.

Example 10 Production of Olefin

A raw material that is a mixture of polyethylene (LDPE) (manufactured by Sumitomo Chemical Co., Ltd., trade name: SUMIKATHENE G201F) (0.9805 g) that is a polyolefin and polyvinyl chloride (PVC) (manufactured by Shin-Etsu Chemical Co., Ltd., trade name: Shin-Etsu PVC straight polymer TK-1000) (0.0052 g) that is an organochlorine compound. (weight ratio LDPE: PVC=99.5:0.5) was filled in an upstream reaction tube of two glass reaction tubes connected in series, and the zeolite catalyst A (0.2 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the zeolite catalyst A, then the temperature of the downstream reaction tube was lowered to 525° C.

A step of thermally decomposing the raw material was performed at an electric furnace temperature of the upstream reaction tube of 455° C. while flowing nitrogen gas at a flow rate of 10 N mL/min to obtain a thermally decomposed raw material. A step of catalytically cracking the thermally decomposed raw material was performed by introducing the thermally decomposed raw material obtained as described above into a downstream reaction tube set at a temperature $T^2$ of 525° C., and bringing the raw material into contact with the zeolite catalyst A.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected. gaseous catalytic cracking product by gas chromatography, the yield of olefins having 2 to 3 carbon atoms was 34.3% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 40.5% on the basis of the mass of the charged polyethylene. The results are also shown in Table 1.

Finally, the spent zeolite catalyst (spent zeolite catalyst M) was collected.

Example 11 Regeneration of Spent Zeolite Catalyst M (Preparation of Regenerated Catalyst N)

The spent zeolite catalyst M was calcined at a temperature of 550° C. for 5 hours in an air atmosphere using a muffle furnace to obtain a regenerated catalyst N.

Example 12 Production of Olefin by Regenerated Catalyst N

Polyethylene (LDPE) (manufactured by Sumitomo Chemical Co., Ltd., trade name: SUMIKATHENE G201F) (0.82 g) was filled in an upstream reaction tube of two glass reaction tubes connected in series that is a polyolefin as a raw material, and regenerated catalyst N (0.16 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the regenerated catalyst N, then the temperature of the downstream reaction tube was lowered to 525° C. A step of thermally decomposing the raw material was performed at an electric furnace temperature of the upstream reaction tube of 455° C. while flowing nitrogen gas at a flow rate of 10 N mL/min to obtain a thermally decomposed raw material.

A step of catalytically cracking the thermally decomposed raw material was performed by introducing the raw material obtained as described above into a downstream reaction tube set at a temperature $T^2$ of 525° C., and bringing the raw material into contact with the regenerated catalyst N.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 35.0% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 41.5% on the basis of the mass of the charged polyethylene. The results are also shown in Table 1.

Example 13 Production of Olefin

A raw material that is a mixture of polyethylene (LDPE) (manufactured by Sumitomo Chemical Co., Ltd., trade name: SUMIKATHENE G201F) (0.135 g) that is a polyolefin and Polyvinyl chloride (PVC) (manufactured by Shin-Etsu Chemical Co., Ltd., trade name: Shin-Etsu PVC straight polymer TK-1000) (0,015 g) that is an organochlorine compound (weight ratio LDPE: PVC=90:10) was tilled in an upstream reaction tube of two glass reaction tubes connected in series, and the zeolite catalyst A (0.3 g) was filled is a downstream reaction tube.

A cooling trap was connected further downstream of the downstream reaction tube, and a 5 L gas bag was connected downstream of the cooling trap.

Nitrogen gas was flowed from the upstream reaction. tube at a flow rate of 10 N mL/min, and only the downstream reaction tube was heated at 550° C. for 1 hour to perform pretreatment of the zeolite catalyst A, then the temperature of the downstream reaction tube was lowered to 525° C.

A step of thermally decomposing the raw material was performed at an electric furnace temperature of the upstream reaction tube of 455° C. while flowing nitrogen Gas at a flow rate of 10 N mL/min to obtain a thermally decomposed raw material. A step of catalytically cracking the thermally decomposed raw material was performed by introducing the thermally decomposed raw material obtained as described above into a downstream reaction tube set at a temperature $T^2$ of 525° C., and bringing the raw material into contact with the zeolite catalyst A.

The whole amount of the liquid catalytic cracking product obtained 2 hours after the start of heating of the raw material was collected in the cooling trap cooled with ice water, and the whole amount of the gaseous catalytic crack product was collected in the gas bag.

Weights of the collected liquid catalytic cracking product and residues attached to the upstream reaction tube and the downstream reaction tube were measured using a balance.

As a result of analyzing the collected gaseous catalytic cracking product by gas chromatography, the yield of olefins having 2 to 3 carbon atoms was 30.3% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 39.7% on the basis of the mass of the charged polyethylene. The results are also shown in Table 1.

Finally, the spent zeolite catalyst (spent zeolite catalyst O) was collected.

Example 14 Regeneration of Spent Zeolite Catalyst O (Preparation of Regenerated Catalyst P)

The spent zeolite catalyst O was calcined at a temperature of 550° C. for 5 hours in an air atmosphere using a muffle furnace to obtain a regenerated catalyst P.

Example 15 Production of Olefin by Regenerated Catalyst P

Polyethylene (LDPE) (manufactured by Sumitomo Chemical Co., Ltd., trade name: SUMIKATHENE G201F) (1.0 g) was filled in an upstream reaction tube of two glass reaction tubes connected in series that is a polyolefin as a raw material, and regenerated catalyst P (0.2 g) was filled in a downstream reaction tube.

A cooling trap was connected further downstream of the downstream reaction tube, and a 5 L gas bag was connected downstream of the cooling trap.

Nitrogen gas was flowed from the upstream reaction tube at a flow rate of 10 N mL/min, and only the downstream reaction tube was heated at 550° C. for 1 hour to perform pretreatment of the regenerated catalyst P, then the temperature of the downstream reaction tube was lowered to 525° C. A step of thermally decomposing the raw material was performed at an electric furnace temperature of the upstream reaction tube of 455° C. while flowing nitrogen gas at a flow rate of 10 N mL/min to obtain a thermally decomposed raw material.

A step of catalytically cracking the thermally decomposed raw material was performed by introducing the raw material obtained as described above into a downstream reaction tube set at a temperature $T^2$ of 525° C., and bringing the raw material into contact with the regenerated catalyst P.

The whole amount of the liquid catalytic cracking. product obtained 2 hours after the start of heating of the raw material was collected in the cooling trap cooled with ice water, and the whole amount of the gaseous catalytic crack product was collected in the gas bag.

Weights of the collected liquid catalytic cracking product and residue attached to the tube and the downstream reaction tube were measured using a balance.

As a result of analyzing the collected gaseous catalytic cracking product by gas chromatography, the yield of olefins having 2 to 3 carbon atoms was 32.8% on the basis of the mass of the charged polyethylene.

In addition, as a result of correcting the analysis value of the gaseous catalytic cracking product so that the sum of the weights of the gaseous catalytic cracking product, the liquid catalytic cracking product, and the residue was the sum of the weights of the raw material polyethylene and PVC, the yield of the olefins having 2 to 3 carbon atoms was calculated to be 42.8% on the basis of the mass of the charged polyethylene. The results are also shown in Table 1.

TABLE 1

|  | Example 1 | Example 3 | Comparative Example 1 | Comparative Example 3 |
|---|---|---|---|---|
| Na Content (% by mass) | <0.01 | — | 0.24 | — |
| Si/Al Ratio | 349 | — | 85 | — |
| Weight ratio of raw materials (%) | LDPE (95) PVC (5) | LDPE (100) | LDPE (95) PVC (5) | LDPE (100) |
| Yield of olefins having 2 to 3 carbon atoms (%) | 37.1 | 39.0 | 19.8 | 26.2 |
| Corrected yield (%) | 34.4 | 36.8 | 25.2 | 30.8 |

|  | Example 4 | Example 6 | Example 7 | Example 9 |
|---|---|---|---|---|
| Na Content (% by mass) | 0.03 | — | <0.01 | — |
| Si/Al Ratio | 576 | — | 1249 | — |

TABLE 1-continued

| | | | | |
|---|---|---|---|---|
| Weight ratio of raw materials (%) | LDPE (95) PVC (5) | LDPE (100) | LDPE (95) PVC (5) | LDPE (100) |
| Yield of olefins having 2 to 3 carbon atoms (%) | 37.0 | 37.5 | 31.2 | 29.8 |
| Corrected yield (%) | 38.8 | 38.6 | 34.5 | 33.2 |

| | Example 10 | Example 12 | Example 13 | Example 15 |
|---|---|---|---|---|
| Na Content (% by mass) | <0.01 | — | <0.01 | — |
| Si/Al Ratio | 349 | — | 349 | — |
| Weight ratio of raw materials (%) | LDPE (99.5) PVC (0.5) | LDPE (100) | LDPE (90) PVC (10) | LDPE (100) |
| Yield of olefins having 2 to 3 carbon atoms (%) | 34.3 | 35.0 | 30.3 | 32.8 |
| Corrected yield (%) | 40.5 | 41.5 | 39.7 | 42.8 |

The invention claimed is:

1. An olefin production method, comprising a step of catalytically cracking a raw material containing at least a polyolefin and an organochlorine compound in the presence of a zeolite catalyst having a sodium atom content of less than 0.1% by mass and a step of thermally decomposing the raw material before the step of catalytically cracking.

2. The olefin production method according to claim 1, wherein the zeolite catalyst is an MFI zeolite catalyst.

3. The olefin production method according to claim 1, wherein the zeolite catalyst has a Si/Al ratio of 100 or more.

4. The olefin production method according to claim 1, wherein the zeolite catalyst has a Si/Al ratio of 300 or more.

5. The olefin production method according to claim 1, wherein the olefins are olefins having 2 to 3 carbon atoms.

6. The olefin production method according to claim 1, wherein the zeolite catalyst has a sodium atom content of less than 0.05% by mass.

7. The olefin production method according to claim 1, wherein the organochlorine compound contains at least one of polyvinyl chloride and polyvinylidene chloride.

8. The olefin production method according to claim 7, wherein the raw material has a chlorine atom content of 10% by mass or less.

9. The olefin production method according to claim 1, further comprising a step of vaporizing the raw material before the step of catalytically cracking, wherein the step of catalytically cracking is a step of catalytically cracking the raw material in a gaseous state.

10. The olefin production method according to claim 1, wherein the step of catalytically cracking is performed at 450° C. or more and 600° C. or less.

11. The olefin production method according to claim 1, wherein the zeolite catalyst is a regenerated catalyst.

12. A method for regenerating a catalyst, comprising a step of calcining the spent zeolite catalyst used in the olefin production method according to claim 1 in an atmosphere containing 1% by volume to 50% by volume of oxygen to obtain a regenerated catalyst.

13. An olefin production method, comprising a step of catalytically cracking a raw material containing a polyolefin in the presence of a regenerated catalyst regenerated by the regeneration method according to claim 12.

* * * * *